United States Patent
Koenemann et al.

(10) Patent No.: US 8,071,775 B2
(45) Date of Patent: Dec. 6, 2011

(54) SUBSTITUTED RYLENE DERIVATIVES

(75) Inventors: Martin Koenemann, Mannheim (DE); Arno Boehm, Mannheim (DE); Neil Gregory Pschirer, Mainz (DE); Jianqiang Qu, Ludwigshafen (DE); Gabriele Mattern, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 971 days.

(21) Appl. No.: 11/994,719

(22) PCT Filed: Jul. 6, 2006

(86) PCT No.: PCT/EP2006/063955
§ 371 (c)(1),
(2), (4) Date: Jan. 4, 2008

(87) PCT Pub. No.: WO2007/006717
PCT Pub. Date: Jan. 18, 2007

(65) Prior Publication Data
US 2008/0167467 A1    Jul. 10, 2008

(30) Foreign Application Priority Data
Jul. 11, 2005 (DE) .......... 10 2005 032 583

(51) Int. Cl.
*C07D 471/08* (2006.01)
*H01L 51/50* (2006.01)

(52) U.S. Cl. ........... 546/26; 313/504; 546/37; 8/115.59; 252/301.16

(58) Field of Classification Search ........ 546/26, 546/37; 313/504; 252/301.16; 8/115.59
See application file for complete search history.

(56) References Cited

U.S. PATENT DOCUMENTS

| | | | | |
|---|---|---|---|---|
| 6,326,494 B1 * | 12/2001 | Bohm et al. | ........... | 546/37 |
| 7,521,556 B2 * | 4/2009 | Boehm et al. | ........... | 546/26 |

FOREIGN PATENT DOCUMENTS

| | | |
|---|---|---|
| DE | 10 2004 057 585 A1 | 6/2006 |
| DE | 10 2005 018 241 A1 | 10/2006 |
| DE | 10 2005 021 362 A1 | 11/2006 |
| WO | WO 96/22332 | 7/1996 |
| WO | WO 97/22607 | 6/1997 |
| WO | WO 02/14414 A2 | 2/2002 |
| WO | WO 02/076988 A2 | 10/2002 |
| WO | WO 03/104232 A1 | 12/2003 |

OTHER PUBLICATIONS

U.S. Appl. No. 12/666,127, filed Dec. 22, 2009, Koenemann, et al.

\* cited by examiner

Primary Examiner — Charanjit Aulakh
(74) Attorney, Agent, or Firm — Oblon, Spivak, McClelland, Maier & Neustadt, L.L.P.

(57) ABSTRACT

Rylene derivatives of the general formula I

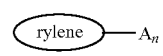

in which the variables are each defined as follows:
Rylene is a polycyclic conjugated ring system which comprises at least one perylene unit

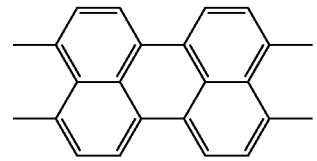

may comprise heteroatoms as ring atoms, may be functionalized by moieties comprising —CO— groups and/or may bear further substituents other than the A radicals;
A is a radical of the formula

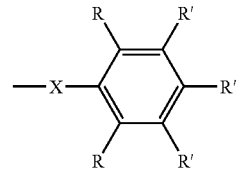

X is oxygen or sulfur;
R are identical or different radicals:
  optionally substituted alkyl, cycloalkyl, aryl, hetaryl, —U-aryl where U is an —O—, —S—, —NR$^2$—, —CO—, —SO— or —SO$_2$— moiety, or C$_1$-C$_{12}$-alkoxy, C$_1$-C$_6$-alkylthio, —C≡CR$^2$, —CR$^2$=CR$^2_2$, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$ or —SO$_3$R$^3$;
R' are identical or different radicals: hydrogen or one of the R radicals;
R$^2$ is hydrogen or alkyl, where the R$^2$ radicals may be the same or different when they occur more than once;
R$^3$, R$^4$ are each independently hydrogen; optionally substituted alkyl, aryl or hetaryl;
n is from 1 to 8.

27 Claims, No Drawings

SUBSTITUTED RYLENE DERIVATIVES

The present invention relates to novel rylene derivatives of the general formula I

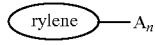

in which the variables are each defined as follows:
rylene is a polycyclic conjugated ring system which comprises at least one perylene unit

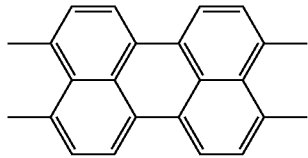

may comprise heteroatoms as ring atoms, may be functionalized by moieties comprising —CO— groups and/or may bear further substituents other than the A radicals;
A is a radical of the formula

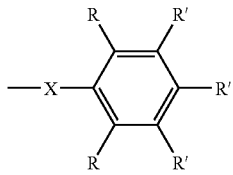

where the A radicals may be the same or different when n>1;
X is oxygen or sulfur;
R are identical or different radicals:
(i) $C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by: $C_1$-$C_{12}$-alkoxy, $C_1$-$C_6$-alkylthio, —C≡CR$^2$, —CR$^2$=CR$^2{}_2$, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$, —SO$_3$R$^3$, saturated or unsaturated $C_4$-$C_7$-cycloalkyl whose carbon skeleton may be interrupted by one or more —O—, —S—, —NR$^2$—, —N=CR$^2$—, —CR$^2$=CR$^2$—, —CO—, —SO— and/or —SO$_2$— moieties, and/or aryl, where aryl and cycloalkyl may each be mono- or polysubstituted by $C_1$-$C_{18}$-alkyl and/or the above radicals mentioned as substituents for alkyl,
where no more than one alkyl radical R may have a tertiary carbon atom in the 1-position;
(ii) $C_3$-$C_8$-cycloalkyl whose carbon skeleton may be interrupted by one or more —O—, —S—, —NR$^2$—, —N=CR$^2$—, —CR$^2$=CR$^2$—, —CO—, —SO— and/or —SO$_2$— moieties and to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^2$, —CR$^2$=CR$^2{}_2$, hydroxy, mercapto, halogen, cyano, nitro, —NR$^3$R$^4$, —NR$^3$COR$^4$, —CONR$^3$R$^4$, —SO$_2$NR$^3$R$^4$ and/or —COOR$^3$,
where no more than one cycloalkyl radical R may have a teritiary carbon atom in the 1-position;
(iii) aryl or hetaryl, to each of which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^2$, —CR$^2$=CR$^2{}_2$, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$, —SO$_3$R$^3$, aryl and/or heteroaryl, each of which may be mono- or polysubstituted by $C_1$-$C_{18}$-alkyl, $C_1$-$C_{12}$-alkoxy, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$ and/or —SO$_3$R$^3$;
(iv) a —U-aryl radical which may be mono- or polysubstituted by the above radicals specified as substituents for the aryl radicals (iii), where U is an —O—, —S—, —NR$^2$—, —CO—, —SO— or —SO$_2$— moiety;
(v) $C_1$-$C_{12}$-alkoxy, $C_1$-$C_6$-alkylthio, —C≡CR$^2$, —C$^2$=CR$^2$, —CR$^2$=CR$^2{}_2$, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$ or —SO$_3$R$^3$;
R' are identical or different radicals:
hydrogen;
one of the radicals specified for R (i), (ii), (iii), (iv) and (v), where the alkyl radicals (i) and the cycloalkyl radicals (ii) may have a tertiary carbon atom in the 1-position;
$R^2$ is hydrogen or $C_1$-$C_{18}$-alkyl, where the $R^2$ radicals may be the same or different when they occur more than once;
$R^3$, $R^4$ are each independently hydrogen;
$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxy, mercapto, halogen, cyano, nitro and/or —COOR$^2$;
aryl or hetaryl, to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by $C_1$-$C_{12}$-alkyl and/or the above radicals specified as substituents for alkyl;
n is from 1 to 8.

The invention also relates to the use of rylene derivatives I for coloring high molecular weight organic and inorganic materials, for producing aqueous polymer dispersions which absorb and/or emit electromagnetic radiation, for obtaining markings and inscriptions which absorb infrared light and are invisible to the human eye, as infrared absorbers for heat management, as IR laser beam-absorbent materials in the fusion bonding of plastics parts, for laser marking and laser inscription, as semiconductors in organic electronics, as filters and emitters in display applications, as emitters in chemiluminescence applications, as labeling groups in detection methods and as active components in photovoltaics.

Perylenetetracarboximides, perylenedicarboximides, the corresponding acid anhydrides and the higher homologs of these compounds are of particular interest especially as fluorescent dyes and as NIR absorbers.

To increase their solubility in the application media, phenoxy or thiophenoxy substituents are typically introduced into the rylene skeleton of these compounds. They are especially unsubstituted or p-substituted, for example by tert-alkyl, phenoxy or thiophenoxy radicals (WO-A-97/22607, WO-A-03/104232, WO-A-96/22332, WO-A-02/76988 and also the prior German applications 10 2005 018 241.0 and 10 2005 021 362.6).

Moreover, WO-A-02/14414 describes perylenetetracarboximides which enable the formation of star-shaped polymers. Their perylene skeleton is substituted by phenoxy radicals which in turn bear reactive groups in the para position.

Finally, the prior German patent application 10 2004 057 585.1 describes rylenetetracarboximides whose rylene skeleton is substituted by cyclic amino groups which bring about a bathochromic shift in the absorption of the diimides.

It was an object of the present invention to further improve the optical properties of rylene derivatives, especially also to increase the steepness of their absorption band.

Accordingly, the rylene derivatives of the formula I defined at the outset have been found.

Also found have been preferred rylene derivatives in which the variables in formula I are each defined as follows:

R are identical or different radicals:
(i) $C_1$-$C_{30}$-alkyl which does not have a tertiary carbon atom in the 1-position and whose carbon chain may be interrupted by one or more —O—, —S—, —$NR^2$—, —C≡C—, —$CR^2$=$CR^2$— and/or —CO— moieties and which may be mono- or polysubstituted by $C_1$-$C_{12}$-alkoxy, hydroxy and/or halogen;
(ii) $C_3$-$C_8$-cycloalkyl which does not have a tertiary carbon atom in the 1-position and whose carbon skeleton may be interrupted by one or more —O—, —S—, —$NR^2$—, —$CR^2$=$CR^2$— and/or —CO— moieties and which may be mono- or polysubstituted by $C_1$-$C_{18}$-alkyl, $C_1$-$C_{12}$-alkoxy and/or $C_1$-$C_6$-alkylthio;
(iii) aryl or hetaryl, to each of which may be fused further saturated or unsaturated 5- to 7-membered rings whose carbon skeleton may be interrupted by one or more —O—, —S—, —$NR^2$—, —N=$CR^2$—, —$CR^2$=$CR^2$—, —CO—, —SO— and/or —$SO_2$— moieties, where the entire ring system may be mono- or polysubstituted by $C_1$-$C_{18}$-alkyl, $C_1$-$C_{12}$-alkoxy, —C≡$CR^2$, —$CR^2$=$CR^2{}_2$, hydroxy, halogen, —$NR^3R^4$, —$NR^3COR^4$, —$CONR^3R^4$, —$SO_2NR^3R^4$, —$COOR^3$ and/or —$SO_3R^3$;
(iv) a —U-aryl radical which may be mono- or polysubstituted by the above radicals specified as substituents for the aryl radicals (iii), where U is an —O—, —S—, —$NR^2$—, —CO—, —SO— or —$SO_2$— moiety;
(v) $C_1$-$C_{12}$-alkoxy, $C_1$-$C_6$-alkylthio, —C≡$CR^2$, —$CR^2$=$CR^2{}_2$, hydroxy, mercapto, halogen, cyano, nitro, —$NR^3R^4$, —$NR^3COR^4$, —$CONR^3R^4$, —$SO_2NR^3R^4$, —$COOR^3$ or —$SO_3R^3$;

R' are identical or different radicals:
hydrogen;
one of the radicals specified for R (i), (ii), (iii), (iv) and (v), where the alkyl radicals (i) and the cycloalkyl radicals (ii) may have a tertiary carbon atom in the 1-position;

$R^2$ is hydrogen or $C_1$-$C_{18}$-alkyl;
$R^3$, $R^4$ are each independently hydrogen;
$C_1$-$C_{18}$-alkyl which may be mono- or polysubstituted by $C_1$-$C_6$-alkoxy, hydroxy, halogen and/or cyano;
aryl or hetaryl, each of which may be mono- or polysubstituted by $C_1$-$C_6$-alkyl and/or the above radicals specified as substituents for alkyl;

n is from 1 to 6.

Finally, particularly preferred rylene derivatives of the formula I have the following definitions of the variables:
A is a radical of the formula

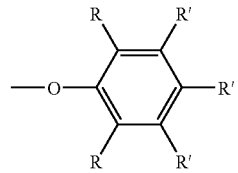

where the A radicals are the same when n>1;
R are identical or different radicals:
(i) $C_1$-$C_{18}$-alkyl which does not have a tertiary carbon atom in the 1-position and whose carbon chain may be interrupted by one or more —O—, —S—, —$NR^2$— and/or —CO— moieties and which may be mono- or polysubstituted by $C_1$-$C_{12}$-alkoxy, hydroxy and/or halogen;
(ii) $C_3$-$C_8$-cycloalkyl which does not have a tertiary carbon atom in the 1-position and may be mono- or polysubstituted by $C_1$-$C_{18}$-alkyl and/or $C_1$-$C_{12}$-alkoxy;
(iii) aryl or hetaryl, each of which may be mono- or polysubstituted by $C_1$-$C_{18}$-alkyl, $C_1$-$C_{12}$-alkoxy, hydroxy and/or halogen;
(iv) a —U-aryl radical which may be mono- or polysubstituted by the above radicals specified as substituents for the aryl radicals (iii), where U is an —O—, —S— or —$NR^2$— moiety;
(v) $C_1$-$C_{12}$-alkoxy, hydroxy, halogen or cyano;

R' are identical or different radicals:
hydrogen;
one of the radicals specified for R (i), (ii), (iii), (iv) and (v), where the alkyl radicals (i) and the cycloalkyl radicals (ii) may comprise a tertiary carbon atom in the 1-position;

$R^2$ is hydrogen or $C_1$-$C_6$-alkyl;
$R^3$, $R^4$ are each independently hydrogen;
$C_1$-$C_{18}$-alkyl which may be mono- or polysubstituted by $C_1$-$C_6$-alkoxy, hydroxy, halogen and/or cyano;
aryl or hetaryl, each of which may be mono- or polysubstituted by $C_1$-$C_6$-alkyl and/or the above radicals specified as substituents for alkyl;

n is from 1 to 6.

The inventive rylene derivatives I have a polycyclic conjugated ring system which comprises at least one perylene unit

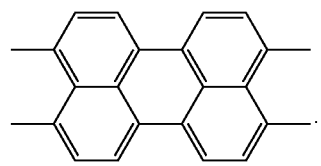

The polycyclic conjugated ring system may comprise heteroatoms as ring atoms. Examples of these heteroatoms are nitrogen, oxygen and sulfur atoms.

Moreover, the ring system may be functionalized by moieties comprising —CO— groups.

The ring system may have one or more functionalizing moieties. When more than one functionalizing moiety is present, they may be the same or different.

Preferred examples of these functionalizing moieties are, in addition to the —CO— group itself,

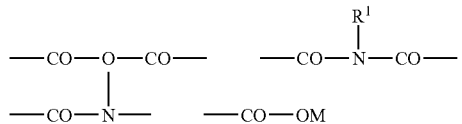

The variable $R^1$ is defined as follows:
hydrogen;
$C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by the radicals specified for R (ii), (iii), (iv) and/or (v); $C_3$-$C_8$-cycloalkyl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the radicals specified for R (i), (ii), (iii), (iv) and/or (v);
aryl or hetaryl, to each of which may be fused further saturated or unsaturated, 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the radicals specified for R (i), (ii), (iii), (iv), (v) and/or aryl- and/or hetarylazo, each of which may be substituted by $C_1$-$C_{10}$-alkyl, $C_1$-$C_6$-alkoxy and/or cyano.
$R^2$, and also $R^3$ and $R^4$, here are each as defined in claim 1.
$R^1$ is preferably defined as follows:
hydrogen;
$C_1$-$C_{30}$-alkyl whose carbon chain may be interrupted by one or more —O— and/or —CO— moieties and which may be mono- or polysubstituted by: $C_1$-$C_6$-alkoxy, cyano and/or aryl which may be mono- or polysubstituted by $C_1$-$C_{18}$-alkyl and/or $C_1$-$C_6$-alkoxy; $C_5$-$C_8$-cycloalkyl which may be mono- or polysubstituted by $C_1$-$C_{12}$-alkyl;
phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —CONR$^3$R$^4$, —SO$_2$NR$^3$R$^4$ and/or phenyl- and/or naphthylazo, each of which may be mono- or polysubstituted by $C_1$-$C_{10}$-alkyl, $C_1$-$C_6$-alkoxy and/or cyano.
$R^3$ and $R^4$ are each as defined in claim 2 and above for preferred rylene derivatives I.
More preferably, $R^1$ is:
hydrogen;
$C_1$-$C_{30}$-alkyl whose carbon chain may be interrupted by one or more —O— and/or —CO—moieties and which may be mono- or polysubstituted by: $C_1$-$C_6$-alkoxy, cyano and/or aryl which may be mono or polysubstituted by $C_1$-$C_{18}$-alkyl and/or $C_1$-$C_6$-alkoxy; $C_5$-$C_8$-cycloalkyl which may be mono- or polysubstituted by $C_1$-$C_6$-alkyl;
phenyl, naphthyl, pyridyl or pyrimidyl, each of which may be mono- or polysubstituted by: $C_1$-$C_{18}$-alkyl, $C_1$-$C_6$-alkoxy, halogen, cyano, nitro, —CONR$^3$R$^4$, —SO$_2$NR$^3$R$^4$ and/or phenyl- and/or naphthylazo, each of which may be mono- or polysubstituted by $C_1$-$C_{10}$-alkyl, $C_1$-$C_6$-alkoxy and/or cyano.
$R^3$ and $R^4$ are each as defined in claim 3 and above for particularly preferred rylene derivatives I.
Very particularly preferred $R^1$ radicals are ortho,ortho'-dialkyl-substituted aryl radicals, in particular those which are also part of the A radical, or linear alkyl chains which are bonded to the imide nitrogen atom via an internal carbon atom. Selected examples of these $R^1$ radicals are 2,6-dimeth-ylphenyl, 2,6-diisopropylphenyl, 2,6-diisopropyl-4-butylphenyl, 5-undecyl, 7-tridecyl and 9-pentadecyl.

Finally, M is hydrogen, an alkali metal cation, NH$_4^+$ or NR$^3_4{}^+$, particular preference being given to alkali metal cations such as lithium, sodium, potassium or cesium cations.

Examples of preferred rylene derivatives I include perylene, terrylene, quaterrylene, pentarylene and hexarylene derivatives.

Examples of the generally preferred functionalized rylene derivatives are:
perylene-3,4:9,10-tetracarboximides, perylenetetracarboxylic acids, their salts and anhydrides, perylenetetracarboxylic monoimide monoanhydrides and condensation products of perylenetetracarboxylic acids/dianhydrides or perylenetetracarboxylic monoimide monoanhydrides with aromatic α,ω-diamines, especially with 1,2-diaminobenzene and 1,8-diaminonaphthalene derivatives;
terrylene-3,4:11,12-tetracarboximides, terrylenetetracarboxylic acids, their salts and anhydrides, terrylenetetracarboxylic monoimide monoanhydrides and condensation products of terrylenetetracarboxylic acids/dianhydrides or terrylenetetracarboxylic monoimide monoanhydrides with aromatic α,ω-diamines, especially with 1,2-diaminobenzene and 1,8-diaminonaphthalene derivatives;
quaterrylene-3,4:13,14-tetracarboximides, quaterrylenetetracarboxylic acids, their salts and anhydrides, quaterrylenetetracarboxylic monoimide monoanhydrides and condensation products of quaterrylenetetracarboxylic acids/dianhydrides or quaterrylenetetracarboxylic monoimide monoanhydrides with aromatic α,ω-diamines, especially with 1,2-diaminobenzene and 1,8-diaminonaphthalene derivatives;
pentarylene-3,4:15,16-tetracarboximides and hexarylene-3,4:17,18-tetracarboximides;
perylene-3,4-dicarboximides and perylenedicarboxylic acids, their salts, anhydrides and condensation products with aromatic α,ω-diamines, especially with 1,2-diaminobenzene and 1,8-diaminonaphthalene derivatives;
terrylene-3,4-dicarboximides and terrylenedicarboxylic acids, their salts, anhydrides and condensation products with aromatic α,ω-diamines, especially with 1,2-diaminobenzene and 1,8-diaminonaphthalene derivatives;
quaterrylene-3,4-dicarboximides and quaterrylenedicarboxylic acids, their salts, anhydrides and condensation products with aromatic α,ω-diamines, especially with 1,2-diaminobenzene and 1,8-diaminonaphthalene derivatives.

The condensation products of the rylenetetracarboxylic acids or of the rylenetetracarboxylic dianhydrides may be mono- or dicondensation products. The dicondensation products may be present in symmetric or asymmetric form; generally, mixtures of both forms are present.

Particular preference is given to the rylenetetracarboximides and rylenedicarboximides mentioned, very particular preference being given to the rylenetetracarboximides.

The inventive rylene derivatives I are substituted by at least one radical A of the formula

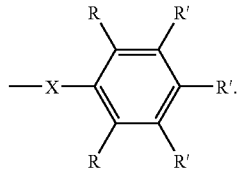

The (thio)phenoxy radicals A are substituted by R radicals in both ortho positions. The two R radicals may be the same or different, but are preferably the same.

The (thio)phenoxy radicals A may also be substituted in one, two or all three further ring positions by identical or different R' radicals other than hydrogen. Preference is given to additional substitution in the para position.

The R radicals may, as detailed at the outset, be alkyl radicals (i) and cycloalkyl radicals (ii), where no more than one of the radicals may have a tertiary carbon atom in the 1-position, but preferably none of the radicals has a tertiary carbon atom in the 1-position, aryl or hetaryl radicals (iii) which may be bonded to the (thio)phenoxy radical via an —O—, —S— or —NR$^2$— moiety, or the substituents (v).

Possible R' radicals correspond to the R radicals, where alkyl radicals and cycloalkyl radicals here may also have tertiary carbon atoms in the 1-position without restriction.

Preferred R (and R') radicals are to be taken from claim 2 and particularly preferred R (and R') radicals from claim 3.

Very particularly R' radicals in this case are the alkyl, cycloalkyl and phenyl radicals, in particular the alkyl radicals R' having a secondary carbon atom in the 1-position, and also methyl and the cycloalkyl radicals R' having a secondary carbon atom in the 1-position, particular emphasis being given to the alkyl and cycloalkyl radicals having a secondary carbon atom in the 1-position.

Examples of the R and R' and also R$^2$ to R$^4$ radicals occurring in the inventive formulae are listed below.

Examples of very particularly preferred A radicals are:
2,6-dimethylphenoxy, 2,6-diethylphenoxy, 2,6-diisopropylphenoxy, 2,6-di(2-butyl)-phenoxy, 2,6-di(n-butyl)phenoxy, 2,6-di(2-hexyl)phenoxy, 2,6-di(n-hexyl)phenoxy, 2,6-di(2-dodecyl)phenoxy, 2,6-di(n-dodecyl)phenoxy, 2,6-dicyclohexylphenoxy, 2,6-diphenyl-phenoxy, 2,6-dimethyl-4-(n-butyl)phenoxy, 2,6-diethyl-4-(n-butyl)phenoxy, 2,6-diisopropyl-4-(n-butyl)-phenoxy, 2,6-di(2-butyl)-4-(n-butyl)phenoxy, 2,4,6-tri(n-butyl)phenoxy, 2,6-di(2-hexyl)-4-(n-butyl)phenoxy, 2,6-di(n-hexyl)-4-(n-butyl)phenoxy, 2,6-di(2-dodecyl)-4-(n-butyl)-phenoxy, 2,6-di(n-dodecyl)-4-(n-butyl)phenoxy, 2,6-dicyclohexyl-4-(n-butyl)phenoxy, 2,6-diphenyl-4-(n-butyl)phenoxy, 2,6-dimethyl-4-(n-nonyl)phenoxy, 2,6-diethyl-4-(n-nonyl)phenoxy, 2,6-diisopropyl-4-(n-nonyl)phenoxy, 2,6-di(2-butyl)-4-(n-nonyl)phenoxy, 2,6-di(2-butyl)-4-(n-nonyl)phenoxy, 2,6-di(2-hexyl)-4-(n-nonyl)phenoxy, 2,6-di(n-hexyl)-4-(n-nonyl)phenoxy, 2,6-di(2-dode-cyl)-4-(n-nonyl)phenoxy, 2,6-di(n-dodecyl)-4-(n-nonyl)phenoxy, 2,6-dicyclohexyl-4-(n-nonyl)phenoxy, 2,6-diphenyl-4-(n-nonyl)phenoxy, 2,6-dimethyl-4-(n-octadecyl)phenoxy, 2,6-diethyl-4-(n-octadecyl)-phenoxy, 2,6-diisopropyl-4-(n-octadecyl)phenoxy, 2,6-di(2-butyl)-4-(n-octadecyl) phen-oxy, 2,6-di(2-butyl)-4-(n-octadecyl)phenoxy, 2,6-di (2-hexyl)-4-(n-octadecyl)phenoxy, 2,6-di(n-hexyl)-4-(n-octadecyl)phenoxy, 2,6-di(2-dodecyl)-4-(n-octadecyl) phenoxy, 2,6-di(n-dodecyl)-4-(n-octadecyl)phenoxy, 2,6-dicyclohexyl-4-(n-octadecyl)phenoxy, 2,6-dimethyl-4-(tert-butyl)phenoxy, 2,6-diethyl-4-(tert-butyl)phenoxy, 2,6-diisopropyl-4-(tert-butyl)phenoxy, 2,6-di(2-butyl)-4-(tert-butyl)phenoxy, 2,6-di-(n-butyl)-4-(tert-butyl)phenoxy, 2,6-di(2-hexyl)-4-(tert-butyl)phenoxy, 2,6-di(n-hexyl)-4-(tert-butyl)-phenoxy, 2,6-di(2-dodecyl)-4-(tert-butyl)phenoxy, 2,6-di(n-dodecyl)-4-(tert-butyl)-phenoxy, 2,6-dicyclohexyl-4-(tert-butyl)phenoxy, 2,6-diphenyl-4-(tert-butyl)phenoxy, 2,6-dimethyl-4-(tert-octyl)phenoxy, 2,6-diethyl-4-(tert-octyl)phenoxy, 2,6-diisopropyl-4-(tert-octyl)phenoxy, 2,6-di(2-butyl)-4-(tert-octyl)phenoxy, 2,6-di-(n-butyl)-4-(tert-octyl)phenoxy, 2,6-di(2-hexyl)-4-(tert-octyl)phenoxy, 2,6-di(n-hexyl)-4-(tert-octyl)phenoxy, 2,6-di(2-dodecyl)-4-(tert-octyl)phenoxy, 2,6-di(n-dode-cyl)-4-(tert-octyl)phenoxy, 2,6-dicyclohexyl-4-(tert-octyl)phenoxy and 2,6-diphenyl-4-(tert-octyl)phenoxy;
2,6-dimethylthiophenoxy, 2,6-diethylthiophenoxy, 2,6-diisopropylthiophenoxy, 2,6-di(2-butyl)thiophenoxy, 2,6-di (n-butyl)thiophenoxy, 2,6-di(2-hexyl)thiophenoxy, 2,6-di (n-hexyl)thiophenoxy, 2,6-di(2-dodecyl)thiophenoxy, 2,6-di(n-dodecyl)thiophenoxy, 2,6-dicyclohexylthiophenoxy, 2,6-diphenyl-thiophenoxy, 2,6-dimethyl-4-(n-butyl) thiophenoxy, 2,6-diethyl-4-(n-butyl)thiophenoxy, 2,6-diisopropyl-4-(n-butyl)thiophenoxy, 2,6-di(2-butyl)-4-(n-butyl)-thiophenoxy, 2,4,6-tri(n-butyl)thiophenoxy, 2,6-di (2-hexyl)-4-(n-butyl)thiophenoxy, 2,6-di(n-hexyl)-4-(n-butyl)thiophenoxy, 2,6-di(2-dodecyl)-4-(n-butyl) thiophenoxy, 2,6-di(n-dodecyl)-4-(n-butyl)thiophenoxy, 2,6-dicyclohexyl-4-(n-butyl)thiophenoxy, 2,6-diphenyl-4-(n-nonyl)thiophenoxy, 2,6-dimethyl-4-(n-nonyl)thiophenoxy, 2,6-diethyl-4-(n-nonyl)thiophenoxy, 2,6-diisopropyl-4-(n-nonyl)thiophenoxy, 2,6-di(2-butyl)-4-(n-nonyl) thiophenoxy, 2,6-di(2-butyl)-4-(n-nonyl)thiophenoxy, 2,6-di(2-hexyl)-4-(n-nonyl)thiophenoxy, 2,6-di(n-hexyl)-4-(n-nonyl)-thiophenoxy, 2,6-di(2-dodecyl)-4-(n-nonyl) thiophenoxy, 2,6-di(n-dodecyl)-4-(n-nonyl)-thiophenoxy, 2,6-dicyclohexyl-4-(n-nonyl)thiophenoxy, 2,6-diphenyl-4-(n-nonyl)thiophenoxy, 2,6-(dimethyl)-4-(n-octadecyl)-thiophenoxy, 2,6-(diethyl)-4-(n-octadecyl)thiophenoxy, 2,6-diisopropyl-4-(n-octadecyl)-thiophenoxy, 2,6-di(2-butyl)-4-(n-octadecyl)thiophenoxy, 2,6-di(2-butyl)-4-(n-octadecyl)thiophenoxy, 2,6-di(2-hexyl)-4-(n-octadecyl) thiophenoxy, 2,6-di(n-hexyl)-4-(n-octadecyl) thiophenoxy, 2,6-di(2-dodecyl)-4-(n-octadecyl) thiophenoxy, 2,6-di(n-dodecyl)-4-(n-octadecyl) thiophenoxy, 2,6-dicyclohexyl-4-(n-octadecyl) thiophenoxy, 2,6-dimethyl-4-(tert-butyl)thiophenoxy, 2,6-diethyl-4-(tert-butyl)thiophenoxy, 2,6-diisopropyl-4-(tert-butyl)thiophenoxy, 2,6-di(2-butyl)-4-(tert-butyl) thiophenoxy, 2,6-di-(n-butyl)-4-(tert-butyl)thiophenoxy, 2,6-di(2-hexyl)-4-(tert-butyl)thiophenoxy, 2,6-di(n-hexyl)-4-(tert-butyl)thiophenoxy, 2,6-di(2-dodecyl)-4-(tert-butyl)thiophenoxy, 2,6-di(n-dodecyl)-4-(tert-butyl) thiophenoxy, 2,6-dicyclohexyl-4-(tert-butyl)thiophenoxy, 2,6-diphenyl-4-(tert-butyl)thiophenoxy, 2,6-dimethyl-4-(tert-octyl)thiophenoxy, 2,6-diethyl-4-(tert-octyl)thiophenoxy, 2,6-diisopropyl-4-(tert-octyl)thiophenoxy, 2,6-di(2-butyl)-4-(tert-octyl)thiophenoxy, 2,6-di-(n-butyl)-4-(tert-octyl)thiophenoxy, 2,6-di(2-hexyl)-4-(tert-octyl) thiophenoxy, 2,6-di(n-hexyl)-4-(tert-octyl)thiophenoxy, 2,6-di(2-dodecyl)-4-(tert-octyl)thiophenoxy, 2,6-di(n-dodecyl)-4-(tert-octyl)thiophenoxy, 2,6-dicyclohexyl-4-(tert-octyl)thiophenoxy and 2,6-diphenyl-4-(tert-octyl) thiophenoxy.

In addition to the inventive A radicals, the rylene derivatives I may also bear further substituents in the rylene skeleton.

Further possible substituents are, for example, (thio)phenoxy radicals Y

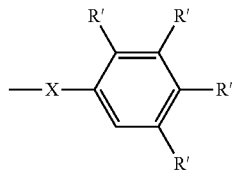

which are not substituted in at least one ortho position and preferably do not bear any substituents at all (R'=H).

Further possible substituents are halogen atoms such as fluorine, chlorine, bromine or iodine, in particular chlorine or bromine. In general, halogen atoms are present in the rylene derivatives I when the halogen atoms introduced first into the rylene skeleton have not been fully replaced by the A (or Y) radicals.

Finally, the rylene derivatives I may also be substituted by cyclic amino groups P.

The substituent P is a 5- to 9-membered ring which is bonded via a nitrogen atom and whose carbon chain may be interrupted by one or more —O—, —S—, —NR$^2$—, —CO— and/or —SO$_2$— moieties, to each of which may be fused one or two unsaturated or saturated 4- to 8-membered rings whose carbon chain may likewise be interrupted by these moieties and/or —N═, where the entire ring system may be mono- or polysubstituted by:

hydroxy, nitro, —NR$^3$R$^4$, —COOR$^3$, —CONR$^3$R$^4$ and/or —NR$^2$COR$^3$;

$C_1$-$C_{30}$-alkyl whose carbon chain may be interrupted by one or more —O—, —S—, —NR$^2$—, —CO— and/or —SO$_2$— moieties and which may be mono- or polysubstituted by cyano, hydroxy, nitro, $C_1$-$C_6$-alkoxy, —COOR$^3$, —CONR$^3$R$^4$, aryl which may be mono- or polysubstituted by $C_1$-$C_{18}$-alkyl and/or $C_1$-$C_6$-alkoxy, and/or a 5- to 7-membered heterocyclic radical which is bonded via a nitrogen atom and may comprise further heteroatoms and be aromatic;

$C_5$-$C_8$-cycloalkyl whose carbon skeleton may be interrupted by one or more —O—, —S— and/or —NR$^2$— moieties and/or which may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, nitro, halogen, —CONR$^3$R$^4$, —NR$^3$COR$^4$, —SO$_3$R$^3$, —SO$_2$NR$^3$R$^4$ and/or aryl- or hetarylazo, each of which may be substituted by $C_1$-$C_{10}$-alkyl, $C_1$-$C_6$-alkoxy or cyano.

P is preferably a 5- to 7-membered ring which is bonded via a nitrogen atom and whose carbon chain may be interrupted by one or more —O—, —S—, —NR$^2$—, —CO— and/or —SO$_2$— moieties, to which may be fused one or two unsaturated or saturated 4- to 8-membered rings whose carbon chain may likewise be interrupted by these moieties and/or —N═, where the entire ring system may be mono- or polysubstituted by $C_1$-$C_{24}$-alkyl, which may be substituted by aryl which may bear $C_1$-$C_{18}$-alkyl as a substituent.

Particularly preferred P radicals are based on the cyclic amines piperidine, pyrrolidine, piperazine, morpholine and thiomorpholine (1,4-thiazine), preference being given to the piperidines, pyrrolidines, piperazines and morpholines, and particular preference to the piperidines.

The cyclic basis amines may be chemically modified, but they are preferably not modified. Examples of chemically modified basis amines include:

piperidine, 2 and 3-methylpiperidine, 6-ethylpiperidine, 2,6- and 3,5-dimethylpiperidine, 2,2,6,6-tetramethylpiperidine, 4-benzylpiperidine, 4-phenylpiperidine, piperidin-4-ol, piperidine-4-carboxylic acid, methyl piperidine-4-carboxylate, ethyl piperidine-4-carboxylate, piperidine-4-carboxamide, 2,2,6,6-tetramethylpiperidin-4-one, 2,2,6,6-tetramethylpiperidin-4-ylamine, decahydroquinoline and decahydroisoquinoline;

pyrrolidine, 2-methylpyrrolidine, 2,5-dimethylpyrrolidine, 2,5-diethylpyrrolidine, tropanol, methylpyrrolidine-2-carboxylate, ethyl pyrrolidine-2-carboxylate, benzyl pyrrolidine-2-carboxylate, pyrrolidine-2-carboxamide, 2,2,5,5-tetramethylpyrrolidine-3-carboxylic acid, methyl 2,2,5,5-tetramethylpyrrolidine-3-carboxylate, ethyl 2,2,5,5-tetramethylpyrrolidine-3-carboxylate, benzyl 2,2,5,5-tetramethylpyrrolidine-3-carboxylate, pyrrolidin-3-ylamine, (2,6-dimethylphenyl)pyrrolidin-2-ylmethylamine, (2,6-diisopropylphenyl)pyrrolidin-2-ylmethylamine and dodecahydrocarbazole;

piperazine, diketopiperazine; 1-benzylpiperazine, 1-phenethylpiperazine, 1-cyclohexylpiperazine, 1-phenylpiperazine, 1-(2,4-dimethylphenyl)piperazine, 1-(2-, 3- and 4-methoxyphenyl)piperazine, 1-(2-, 3- and 4-ethoxyphenyl)piperazine, 1-(2-, 3- and 4-fluorophenyl)piperazine, 1-(2-, 3- and 4-chlorophenyl)piperazine, 1-(2-, 3- and 4-bromophenyl)piperazine, 1-, 2- and 3-pyridin-2-ylpiperazine and 1-benzo[1,3]dioxol-4-ylmethylpiperazine;

morpholine, 2,6-dimethylmorpholine, 3,3,5,5-tetramethylmorpholine, morpholin-2- and -3-ylmethanol, morpholin-2- and -3-ylacetic acid, methyl morpholin-2- and -3-ylacetate, ethyl morpholin-2- and -3-ylacetate, methyl 3-morpholin-3-ylpropionate, ethyl 3-morpholin-3-ylpropionate, tert-butyl 3-morpholin-3-ylpropionate, morpholin-2- and -3-ylacetamide, 3-morpholin-3-ylpropionamide, 3-benzylmorpholine, 3-methyl-2-phenylmorpholine, 2- and 3-phenylmorpholine, 2-(4-methoxyphenyl)morpholine, 2-(4-trifluoromethylphenyl)morpholine, 2-(4-chlorophenyl)-morpholine, 2-(3,5-dichlorophenyl)morpholine, morpholine-2- and -3-carboxylic acid, methyl morpholine-3-carboxylate, 3-pyridin-3-ylmorpholine, 5-phenylmorpholin-2-one, 2-morpholin-2-ylethylamine and phenoxazine;

thiomorpholine, 2- and 3-phenylthiomorpholine, 2- and 3-(4-methoxyphenyl)thiomorpholine, 2- and 3-(4-fluorophenyl)thiomorpholine, 2- and 3-(4-trifluoromethylphenyl)thiomorpholine, 2- and 3-(2-chlorophenyl)thiomorpholine, 4-(2-aminoethyl)thiomorpholine, 3-pyridin-3-ylthiomorpholine, 3-thiomorpholinecarboxylic acid, 6,6-dimethyl-5-oxo-3-thiomorpholinecarboxylic acid, 3-thiomorpholinone and 2-phenylthiomorpholin-3-one, and also the thiomorpholine oxides and dioxides.

Introduction of the substituents P can bring about an additional bathochromic shift in the absorption of the rylene derivatives I.

The substitution of the rylene derivatives I by the radicals listed above will be illustrated in detail using the example of the perylene, terrylene, quaterrylene, pentarylene and hexarylene derivatives.

Thus, the inventive perylene, terrylene and quaterrylene derivatives correspond preferably to the formula Ia

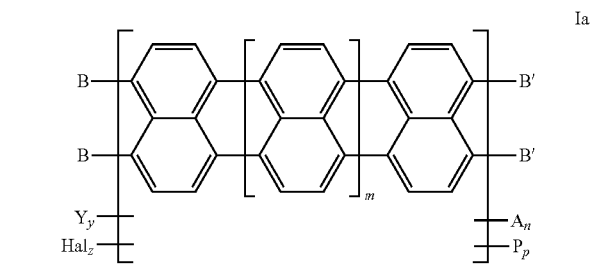

in which the variables not defined above are each defined as follows:

B are joined together with formation of a six-membered ring to give a radical of the formula (a), (b) or (c)

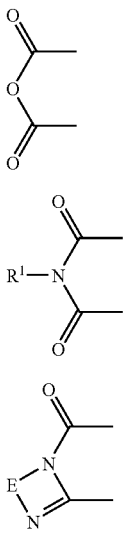

are both hydrogen or a —COOM radical, or one of the two radicals is an A radical or Hal and the other radical is hydrogen;

B', independently of B, are joined together with formation of a six-membered ring to give a radical of the formula (a), (b) or (c), or are both hydrogen or a —COOM radical;

E is 1,2-phenylene, 1,8- or 2,3-naphthylene or 2,3- or 3,4-pyridylene, each of which may be substituted by $C_1$-$C_{12}$-alkyl, $C_1$-$C_6$-alkoxy, hydroxy, nitro and/or halogen, where the E radicals may be the same or different when they occur more than once in formula Ia;

m is 0, 1 or 2;
n is from 1 to 8, in particular form 1 to 6;
p is from 0 to 5 where $n+p \leq 8$; in particular from 1 to 2 where $n+p \leq 6$;
y is from 0 to 5 where $n+p+y \leq 8$; in particular from 0 to 5 where $n+p+y \leq 6$;
z is from 0 to 6 where $n+p+y+z \leq 10$; in particular from 0 to 5 where $n+p+y \leq 6$;

The variables n (number of substituents A), p (number of cyclic amino radicals P), y (number of (thio)phenoxy radicals Y) and z (number of halogen atoms Hal) for the individual rylene derivatives Ia are in particular each defined as follows:

Perylene Derivatives Ia (m=0):
n is from 1 to 4;
p is from 0 to 2 where $n+p \leq 4$;
y is from 0 to 4 where $n+p+y \leq 4$;
z is from 0 to 4 where $n+p+y+z \leq 6$.

Terrylene Derivatives Ia (m=1):
n is from 1 to 6;
p is from 0 to 3 where $n+p \leq 6$;
y is from 0 to 3 where $n+p+y \leq 6$;
z is from 0 to 5 where $n+p+y+z \leq 8$.

Quaterrylene Derivatives Ia (m=2):
n is from 1 to 8;
p is from 0 to 5 where $n+p \leq 8$;
y is from 0 to 5 where $n+p+y \leq 8$;
z is from 0 to 6 where $n+p+y+z \leq 10$.

The following definitions for the variables n, p, y and z are particularly preferred:

Perylene Derivatives Ia (m=0):
n is from 1 to 2;
p is 0;
y is 0;
z is 0.

Terrylene Derivatives Ia (m=1):
n is from 1 to 4;
p is 0;
y is 0;
z is from 0 to 3 where: $n+z \leq 4$.

Quaterrylene Derivatives Ia (m=2):
n is from 1 to 6;
p is 0;
y is 0;
z is from 0 to 5 where: $n+z \leq 6$.

The perylenetetracarboxylic acid derivatives Ia are preferably disubstituted (in particular in the 1,7- or 1,6-position) or tetrasubstituted (in particular in the 1,6,7,12-position) and comprise preferably two A radicals. In the perylenedicarboxylic acid derivatives Ia, an additional substitution of the peri position (9-position), especially by an A radical or a halogen atom, is possible.

The terrylenetetracarboxylic acid derivatives Ia are preferably tetrasubstituted (in particular in the 1,6,9,14-position) and comprise especially at least two A radicals. In the case of the terrylenedicarboxylic acid derivatives too, perisubstitution (11-position), in particular by a halogen atom, is possible.

Finally, the quaterrylenetetracarboxylic acid derivatives Ia are preferably tetrasubstituted (in particular in the 1,6,11,16-position) or hexasubstituted (in particular in the 1,6,8,11,16,18- or 1,6,8,11,16,19-position) and comprise preferably 4 A radicals. Peri-substitution (13-position), especially by a halogen atom, is again additionally possible in the quaterrylenedicarboxylic acid derivatives.

Frequently, the rylene derivatives Ia are obtained in the form of mixtures of products with different degrees of substitution, in which the products specified explicitly above make up the majority in each case.

Particularly preferred rylene derivatives Ia are the perylene-, terrylene- and quatterylenetetracarboximides and the perylene-, terrylene- and quaterrylenedicarboximides, very particular preference being given to the rylenetetracarboximides.

Especially preferred are diimides and monoimides Ia which are substituted on the imide nitrogen atoms by aryl radicals which likewise have ortho,ortho'-disubstitution, i.e. correspond in particular to the phenyl radicals present in the A radicals, since these rylene derivatives Ia exhibit particularly steep absorption bands.

The inventive pentarylene and hexarylene derivatives correspond in particular to the formula Ib

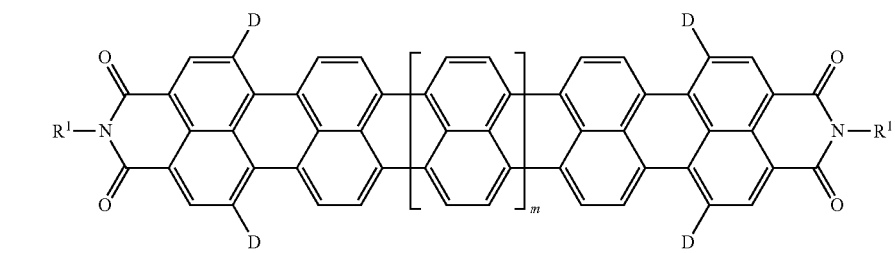

in which the variables D and m are each defined as follows:
D are identical or different radicals:
    hydrogen, an A radical or a Y radical, where at least one of the D radicals is an A radical;
m is 1 or 2.

The pentarylene derivatives and hexarylene derivatives Ib are preferably each tetrasubstituted in the 1,6,13,18-position or 1,6,15,20-position and comprise preferably at least two A radicals.

In general, the rylene derivatives Ib too are obtained in the form of mixtures of products with different degrees of substitution, in which the products specified explicitly above make up the majority in each case.

In the case of the rylene derivatives Ib too, preference is given to the derivatives which are substituted on the imide nitrogen atoms by aryl radicals with ortho,ortho'-disubstitution, since they exhibit distinctly steeper absorption bands.

Finally, examples of the R, R' and $R^1$ to $R^4$ radicals and also their substituents occurring in the inventive formulae include:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The substituents A which characterize the inventive rylene derivatives I may be introduced into the rylene skeleton advantageously by reacting the appropriate halogenated (preferably the chlorinated or in particular brominated) rylene derivatives with ortho,ortho'-disubstituted (thio)phenols HA of the general formula II

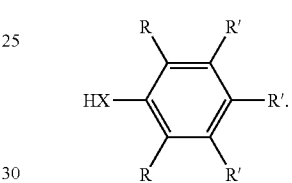

This reaction is appropriately undertaken in the presence of a base and of a non-nucleophilic solvent.

However, the (thio)phenol HA may also be converted beforehand to the (thio)phenoxide. In this case, it is possible to dispense with the presence of a base in the nucleophilic substitution.

In this way, it is also possible by incomplete halogen exchange to obtain rylene derivatives which bear both the A radicals and halogen atoms as substituents on the ring system.

The nucleophilic substitution on the halogenated rylene derivatives also offers the possibility of preparing rylene derivatives I which, in addition to the A radicals, have other additional substituents.

Thus, rylene derivatives I which bear both the A radicals and further (thio)phenoxy radicals Y which are not ortho, ortho'-disubstituted as substituents can be prepared readily by incipient (thio)phenoxylation with one (thio)phenol HA or HY and supplementary reaction with the other (thio)phenol HY or HA in each case, or else parallel reaction with both (thio)phenols.

Rylene derivatives I which have cyclic amino groups P as additional substituents can be obtained analogously, i.e. by incipient (thio)phenoxylation with the ortho,ortho'-disubstituted (thio)phenol HA and supplementary reaction with an amine HP, or first partial reaction with the amine HP and then supplementary (thio)phenoxylation, or else by parallel reaction of the halogenated rylene derivative with HA and HP.

Rylene derivatives I which have combinations of at least 3 different substituents can of course be prepared in a corresponding manner.

The reaction of the halogenated rylene derivatives with the (thio)phenol HA is described in detail below using the example of the perylene-, terrylene- and quaterrylenetetracarboximides and -dicarboximides (referred to below as "rylenecarboximides").

Suitable non-nucleophilic solvents for this reaction are in particular polar aprotic solvents, especially aliphatic carboxamides (preferably N,N-di-$C_1$-$C_4$-alkyl-$C_1$-$C_4$-carboxamides) and lactams such as dimethylformamide, diethylformamide, dimethylacetamide, dimethylbutyramide and N-methylpyrrolidone.

The non-nucleophilic solvents used may also be nonpolar aprotic solvents, but these solvents are not preferred. Examples include aromatic hydrocarbons such as benzene, toluene and xylene.

It would be appreciated that it is also possible to use solvent mixtures.

The amount of solvents depends upon the solubility of the halogenated rylene derivative. In general, from 2 to 200 ml, in particular from 3 to 150 ml of solvent are required per g of halogenated rylene derivative.

Suitable bases are in particular inorganic and organic alkali metal or alkaline earth metal bases, the alkali metal bases being particularly suitable. Examples of inorganic bases are the carbonates and hydrogencarbonates, hydroxides, hydrides and amides of alkali metals and alkaline earth metals; examples of organic bases are alkoxides (especially the $C_1$-$C_{10}$-alkoxides, in particular tert-$C_4$-$C_6$-alkoxides), (phenyl)alkylamides (especially the bis($C_1$-$C_4$-alkyl)amides) and triphenylmethylmetallates based on alkali metals and alkaline earth metals. Preferred bases are the carbonates and hydrogencarbonates, particular preference being given to the carbonates. Preferred alkali metals are lithium, sodium, potassium and cesium; particularly suitable alkaline earth metals are magnesium and calcium.

Specific examples of the metallic bases include: lithium carbonate, sodium carbonate, potassium carbonate and cesium carbonate, sodium hydrogencarbonate and potassium hydrogencarbonate; lithium hydroxide, sodium hydroxide, potassium hydroxide and cesium hydroxide; lithium hydride, sodium hydride and potassium hydride; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide, potassium tert-butoxide, lithium (1,1-dimethyl)octoxide, sodium (1,1-dimethyl)octoxide and potassium (1,1-dimethyl)octoxide; lithium dimethylamide, lithium diethylamide, lithium diisopropylamide, sodium diisopropylamide, lithium hexamethyldisilazide, sodium hexamethyldisilazide, potassium hexamethyldisilazide, triphenylmethyllithium, triphenylmethylsodium and triphenylmethylpotassium.

In addition to these metallic bases, purely organic nitrogen bases are also suitable.

Suitable examples thereof are alkylamines, especially tri($C_2$-$C_6$-alkyl)amines, such as triethylamine, tripropylamine and tributylamine, alcoholamines, especially mono-, di- and tri($C_2$-$C_4$-alcohol)amines, such as mono-, di- and triethanolamine, and heterocyclic bases such as pyridine, 4-(N,N-dimethylamino)pyridine, (4-pyrrolidino)pyridine, N-methylpiperidine, N-methylpiperidone, N-methylmorpholine, N-methyl-2-pyrrolidone, pyrimidine, quinoline, isoquinoline, quinaldine, diazabicyclooctane (DABCO), diazabicyclononene (DBN) and diazabicycloundecene (DBU).

It will be appreciated that it is also possible to use base mixtures.

Very particularly preferred bases are lithium carbonate, sodium carbonate, potassium carbonate and cesium carbonate.

In general, at least 0.4 equivalent of base is required per mole of (thio)phenol HA. Particularly suitable use amounts for the metal bases are from 0.4 to 3 equivalents, especially from 0.4 to 1.2 equivalents per mole of HA. In the case of the purely organic bases, the use amount is preferably from 0.4 to 10 equivalents, more preferably from 0.4 to 3 equivalents per mole of HA. When the organic base is used simultaneously as a solvent, which may be the case especially for the heterocyclic bases, a quantitative restriction is of course superfluous.

The reaction may be undertaken in the presence of phase transfer catalysts.

Suitable phase transfer catalysts are in particular quaternary ammonium salts and phosphonium salts such as tetra($C_1$-$C_{18}$-alkyl)ammonium halides and tetrafluoroborates, benzyltri($C_1$-$C_{18}$-alkyl)ammonium halides and tetrafluoroborates and tetra($C_1$-$C_{18}$-alkyl)- and tetraphenylphosphonium halides, and crown ethers. The halides are generally the fluorides, chlorides, bromides and iodides, preference being given to the chlorides and bromides. Particularly suitable specific examples are: tetraethylammonium chloride, tetrabutylammonium bromide, tetrabutylammonium iodide, tetrabutylammonium tetrafluoroborate and benzyltriethylammonium chloride; tetrabutylphosphonium bromide and tetraphenylphosphonium chloride and bromide; 18-crown-6, 12-crown-4 and 15-crown-5.

When a phase transfer catalyst is used, its use amount is typically from 0.4 to 10 equivalents, in particular from 0.4 to 3 equivalents, per mole of (thio)phenol.

In general, from 1 to 10 mol, preferably from 1 to 5 mol of (thio)phenol HA are used per mole of halogen atom to be exchanged. When the intention is to only partly replace the halogen atoms, it is recommended to lower the amount of (thio)phenol to from 1 to 1.5 mol, preferably from 1 to 1.2 mol per mole of halogen atom to be exchanged.

The reaction temperature depends upon the reactivity of the substrate and is generally within the range from 30 to 150° C.

The reaction time is typically from 0.5 to 96 h, in particular from 2 to 72 h.

In terms of process technology, it is possible to proceed in different ways. It is possible first to mix the reactants and then to heat them together to the reaction temperature. Especially to achieve high degrees of substitution, it may be advantageous to initially charge only a portion of the (thio)phenol HA and of the base and to add the rest only at a later stage, if appropriate after intermediate isolation of the product partly (thio)phenoxylated in the more reactive positions.

The isolation of the resulting rylenecarboximides Ia can be undertaken as follows when inorganic bases are used:

The inorganic salts obtained can first be filtered off, and then the rylenecarboximide Ia precipitated by addition of aliphatic alcohols such as methanol, ethanol, isopropanol, butanol or ethylene glycol monobutyl ether, of water or of water/alcohol mixtures, or by evaporation of the solvent, and subsequently filtered off.

However, the inorganic salts can also be filtered off together with the precipitated rylenecarboximide Ia and washed out by washing with water and/or dilute inorganic acids such as hydrochloric acid or sulfuric acid.

If desired, the resulting rylenecarboximides Ia may be additionally purified by subjecting them to a filtration or column chromatography on silica gel. Suitable eluents are in particular halogenated aliphatic hydrocarbons such as methylene chloride and chloroform, aliphatic and aromatic hydrocarbons such as cyclohexane, petroleum ether, benzene, toluene and xylene, aliphatic alcohols such as methanol and ethanol, and aliphatic carboxylic esters such as ethyl acetate, which are preferably used in the form of mixtures.

In the case of only partly (thio)phenoxylated rylenecarboximides Ia, the halogen still present can be removed if desired.

This can be done advantageously, as described in WO-A-02/76988, by a transition metal-catalyzed reductive dehalogenation in the presence of a solvent inert under the reaction conditions, or in a base-induced manner in the presence of an inert nitrogen-basic or aromatic solvent.

The dehalogenation may be undertaken before the isolation of the reaction product in the reaction mixture obtained in the (thio)phenoxylation. However, the reaction product may, if desired, also first be intermediately isolated and additionally purified if appropriate. The base-induced dehalogenation may also be associated directly with the (thio)phenoxylation, by using strong bases in a larger amount from the outset and heating the reaction mixture to a higher temperature on completion of the (thio)phenoxylation.

Suitable reducing agents for the reductive dehalogenation are in particular complex hydrides, especially borohydrides such as sodium borohydride, and elemental hydrogen.

In the case of the complex hydrides, the amount of reducing agent is generally from 1 to 8 equivalents, preferably from 2 to 5 equivalents per mole of halogen atom to be eliminated.

In the case of reduction with hydrogen, the amount of hydrogen added is sufficient to complete the reaction. It is possible to work at a hydrogen pressure of from 1 to 100 bar, but a hydrogen pressure of around 1 bar will generally be sufficient.

When complex hydrides are used as the reducing agent, suitable transition metal catalysts are especially palladium compounds such as palladium acetate, dichloro(1,5-cyclooctadiene)palladium(II), dichloro[1,1'-bis(diphenylphosphino)ferrocene]palladium(II), tri(dibenzylideneacetone)dipalladium(0), tetrakis(triphenylphosphine)palladium(0) and tetrakis(tris-o-tolylphosphine)palladium(0).

When hydrogen is used as the reducing agent, it is likewise possible to use the abovementioned transition metal catalysts, but preference is given to using palladium on activated carbon.

In general, from 0.5 to 10 mol %, preferably from 0.5 to 5 mol %, of catalyst are used per mole of halogen atom to be eliminated.

Suitable inert solvents are in particular aliphatic carbonitriles such as acetonitrile and propionitrile, aliphatic carboxamides such as N,N-dimethylformamide and N,N-dimethylacetamide, and lactams such as N-methylpyrrolidone.

The amount of solvent is generally from 10 to 100 mol of solvent per g of rylenecarboximide Ia to be dehalogenated.

In the case of reductive dehalogenation with complex hydrides, it is recommended to work under protective gas.

The reaction temperature is typically in the range from 20 to 100° C. when complex hydrides are used and from 20 to 50° C. in the case of reduction with hydrogen.

The reaction time is generally from 5 to 100 h, preferably from 12 to 60 h.

The reductive dehalogenation may be undertaken directly after the (thio)phenoxylation by cooling the reaction mixture to room temperature, adding the reducing agent and the catalyst, and then heating the mixture to the desired reaction temperature. However, the (thio)phenoxylated product can also, if desired, first be intermediately isolated and additionally purified if appropriate.

Suitable bases for the base-induced dehalogenation are in particular alkali metal hydroxides such as potassium hydroxide and sodium hydroxide, alkali metal carbonates such as potassium carbonate, sodium carbonate and cesium carbonate, alkali metal alkoxides of secondary and tertiary alcohols, such as the isopropoxides and tert-butoxides of lithium, sodium and potassium, and also sterically hindered nitrogen bases such as DABCO, DBN and DBU.

In general, from 1 to 3 equivalents, preferably from 1 to 1.5 equivalents, of base are used per mole of halogen atom to be eliminated.

The solvents used may be the same solvents as in the (thio)phenoxylation.

The amount of solvent is appropriately from 2 to 200 ml, especially from 3 to 100 ml, per g of rylenecarboximide Ia to be dehalogenated.

The reaction temperature is typically in the range from 50 to 200° C., preferably from 60 to 130° C.

It is recommended to undertake the dehalogenation under protective gas.

The base-induced dehalogenation has generally ended within from 5 to 72 h, in particular within from 10 to 48 h.

To prepare all inventive functionalized perylene, terrylene and quaterrylene derivatives Ia, the starting materials are preferably the corresponding halogenated rylenetetracarboximides which are described, for example, in WO-A-97/22607, 03/104232 and 96/22332.

After the (thio)phenoxylation, the diimides may then, if desired, be converted by hydrolysis to the rylenetetracarboxylic dianhydrides Ia or the rylenetetracarboxylic monoimide monoanhydrides Ia.

The rylenetetracarboxylic monoimide monoanhydrides Ia may be decarboxylated to the rylenedicarboximides Ia from which the corresponding rylenedicarboxylic anhydrides Ia are obtainable in turn by hydrolysis.

It will be appreciated that the rylenedicarboximide Ia may also, as described above, be prepared by (thio)phenoxylating the halogened rylenedicarboximides.

The rylenetetracarboxylic dianhydrides Ia may be converted by decarboxylation to the unfunctionalized rylenes Ia or by reaction with aromatic diamines $H_2N$-E-$NH_2$ to the corresponding di- and monocondensation products.

Finally, it is also possible to obtain the corresponding rylenetetracarboxylic monoimide semicondensation products from the rylenetetracarboxylic monoimide monoanhydrides Ia by reaction with aromatic diamines $H_2N$-E-$NH_2$.

The consequence of these transfunctionalizations is described using the example of the terrylene and quaterrylene derivatives in prior German patent application 10 2005 021 362.6.

The inventive pentarylene- and hexarylenetetracarboximides Ib are finally obtainable by coupling reaction of perylene- and terrylenedicarboximides substituted by the A radicals (and if desired by the Y radicals), or by homologous coupling of appropriately substituted terrylenedicarboximides. These coupling reactions are described in detail in prior German patent application 10 2005 018 241.0.

The inventive rylene derivatives I are notable for steep absorption bands. They therefore have particularly brilliant absorption and fluorescence hues. In the case of fluorescent inventive rylene derivatives I, the fluorescence quantum yield has also been increased. At the same time, the absorption maxima are shifted to a longer wavelength compared to the corresponding species not substituted by the A radicals in each case, which has the consequence of better utilization of the incident light for many applications.

The inventive rylene derivatives I may be incorporated without any problem into organic and inorganic materials and are therefore suitable for a whole series of end uses, some of which will be listed by way of example below.

They may be used generally for coloring coatings, printing inks and plastics.

The perylene and terrylene derivatives I absorb in the visible region of the electromagnetic spectrum and are notable for their fluorescence which, in the case of the perylene derivatives I, lies within the visible region of the electromagnetic spectrum.

The higher rylene derivatives I are of interest especially owing to their absorption capacity in the near infrared region of the electromagnetic spectrum.

The inventive rylene derivatives I may be used to produce aqueous polymer dispersions which absorb and/or emit electromagnetic radiation. Fluorescent polymer dispersions are obtained with the terrylene derivatives I and especially with the perylene derivatives I, while polymer dispersions absorbing in the near infrared region of the electromagnetic spectrum result with the higher homologs.

Moreover, especially the higher rylene derivatives I are suitable, owing to their pronounced absorption in the near infrared region of the electromagnetic spectrum, for obtaining markings and inscriptions which absorb infrared light and are invisible to the human eye, as infrared absorbers for heat management and as IR laser beam-absorbent materials in the fusion treatment of plastics parts. These applications are described in detail, for example, in DE-A-10 2004 018 547 and WO-A-02/77081 and 04/05427.

The higher rylene derivatives I may also be used advantageously for laser marking and laser inscription. In this case, the laser light absorbed by the rylene derivatives I brings about heating of the plastic, which leads to it foaming or the conversion of a dye present in addition, and in this way gives rise to a marking or inscription.

Moreover, the inventive rylene derivatives I may also be used as semiconductors in organic electronics. Examples of individual applications within this field are field-effect transistors and electrophotography.

The inventive rylene derivatives I can also be used as filters or emitters for display applications. In this case, the fluorescent rylene derivatives I which absorb in the visible region, i.e. in particular the perylene derivatives I, are of interest as absorbent color filters or as fluorescent emitters for LCD and OLED displays, while the higher rylene derivatives I which absorb in the NIR can function in particular as protective filters for NIR radiation.

Finally, the rylene derivatives I may also find use as emitters in chemiluminescence applications. Here, the fluorescent dyes based on perylene and terrylene are again particularly suitable.

The fluorescent dyes based on perylene and terrylene are also of interest as labeling groups in detection methods, especially in diagnostic and analytical methods on biological samples, including living cells.

Finally, the inventive rylene derivatives I, especially the perylene and terrylene derivatives I, may also be used as active components in photovoltaics.

EXAMPLES

Example 1

N,N'-Bis(2,6-diisopropylphenyl)-1,7- and -1,6-bis(2,6-diisopropylphenoxy)-perylene-3,4:9,10-tetracarboximide (Ia1)

1.24 g (9 mmol) of potassium carbonate are added to a mixture of 2.6 g (3 mmol) of a mixture of N,N'-bis(2,6-diisopropylphenyl)-1,7- and -1,6-dibromoperylene-3,4:9,10-tetracarboximide (isomer ratio 75:25) and 1.39 g (7.5 mmol) of 2,6-diisopropylphenol in 150 ml of N-methylpyrrolidone. The mixture was then heated to 95° C. and stirred at this temperature for 4 h. After cooling to room temperature, 150 ml of water were added slowly. After stirring for a further hour, the precipitated product was filtered off, washed successively in portions with a total of 300 ml of 10% by weight sulfuric acid, with water and with a little ethanol, and dried under reduced pressure.

2.4 g (75%) of the rylene derivative mixture Ia1 were obtained in the form of a violet solid which was purified further by subjecting it to column chromatography on silica gel with toluene as the eluent.

Absorption: $\lambda_{max}$ ($CH_2Cl_2$)=557 nm;
Emission: $\lambda_{max}$ ($CH_2Cl_2$)=575 nm.

In comparison to the UV spectrum of a mixture of N,N'-bis(2,6-diisopropylphenyl)-1,7- and -1,6-bis(4-tert-octylphenoxy)perylene-3,4:9,10-tetracarboximide (C1), the UV spectrum of Ia1 exhibits a distinctly steeper absorption band with the absorption maximum shifted to a longer wavelength (C1: $\lambda_{max}$ (absorption) ($CH_2Cl_2$)=543 nm).

The rylene derivative mixture Ia1 and C1 were each incorporated in an amount of 0.02% by weight into PMMA, and processed to an injection molding of edge length 5.5×5.5 cm.

The injection molding comprising the rylene derivative mixture Ia1 had a distinctly higher edge fluorescence and a distinctly more brilliant blue hue.

Example 2

N,N'-Bis(2,6-diisopropylphenyl)-1,6,9,14-tetra(2,6-diisopropylphenoxy)-terrylene-3,4:11,12-tetracarboximide (Ia2)

2.48 g (18 mmol) of potassium carbonate were added to a mixture of 3.45 g (3 mmol) of N,N'-bis(2,6-diisopropylphenyl)-1,6,9,14-tetrabromoterrylene-3,4:11,12-tetracarboximide and 2.8 g (15 mmol) of 2,6-diisopropylphenol in 200 ml of N-methylpyrrolidone. The mixture was then heated to 80° C. and stirred at this temperature for 5 h. After cooling to room temperature, 50 ml of water were added. After stirring for a further 10 hours, the precipitated product was filtered off, washed first in portions with a total of 400 ml of 10% by weight sulfuric acid and then to neutrality with water, and dried under reduced pressure.

4.25 g (92%) of the rylene derivative Ia2 were obtained in the form of a green solid which was purified further by subjecting it to column chromatography on silica gel with toluene as the eluent.

$R_f$ value (8:1 petroleum ether/ethyl acetate)=0.8;
Absorption: $\lambda_{max}$ ($CH_2Cl_2$)=694 nm; material extinction E=90 l g$^{-1}$ cm$^{-1}$;
Emission: $\lambda_{max}$ ($CH_2Cl_2$)=720 nm.

Example 3

N,N'-Bis(2,6-diisopropylphenyl)-1,6,11,16-tetra(2,6-diisopropylphenoxy)-quaterrylene-3,4:13,14-tetracarboximide (Ia3)

2.52 g (18 mmol) of potassium carbonate were added within 4 h to a mixture of 12.9 g (9 mmol) of an approximately equal mixture of N,N'-bis(2,6-diisopropylphenyl)-1,6,8,11,16,18- and -1,6,8,11,16,19-hexabromoquaterrylene-3,4:13,14-tetracarboximide and 8.4 g (45 mmol) of 2,6-diisopropylphenol in 600 ml of N-methylpyrrolidone. The mixture was then heated first to 100° C. and stirred at this temperature for 2 h, then heated to 110° C. for 2 h and finally to 120° C. for 2 h. At this temperature, a further 2.0 g (11 mmol) of 2,6-diisopropylphenol and 0.63 g (4.5 mmol) of potassium carbonate were added. After stirring at 120° C. for a further 5 hours, the mixture was cooled to room temperature.

To dehalogenate the mixture, obtained here as the main component, of N,N'-bis(2,6-diisopropylphenyl)-1,6,11,16-tetra(2,6-diisopropylphenoxy)-8,18- and -8,19-dibromoquaterrylene-3,4:13,14-tetracarboximide, the resulting reaction mixture was admixed with 1.98 g (52 mmol) of sodium borohydride and 0.12 g (0.1 mmol) of tetrakis(triphenylphosphine)palladium(0) and heated to 70° C. for 13 h.

After cooling to room temperature, the product was precipitated by slowly adding first 300 ml of water and then 100 ml of 10% by weight sulfuric acid, filtered off, washed first in portions with a total of 400 ml of 10% by weight sulfuric acid and then to neutrality with water, and dried under reduced pressure.

12.8 g (78%) of the rylene derivative Ia3 were obtained in the form of a green solid which was further purified by subjecting it to column chromatography on silica gel with toluene as the eluent.

$R_f$ value (8:1 petroleum ether/ethyl acetate)=0.5;
Absorption: $\lambda_{max}$ ($CH_2Cl_2$)=802 nm; material extinction $E=98 \, l\,g^{-1}\,cm^{-1}$.

In comparison to the UV spectrum of N,N'-bis(2,6-diisopropylphenyl)-1,6,11,16-tetra(4-tert-octylphenoxy)quaterrylene-3,4:13,14-tetracarboximide (C3), the UV spectrum of Ia3 exhibits a steeper bathochromically shifted absorption band and lower residual absorption in the visible region (C3: $\lambda_{max}$ (absorption) ($CH_2Cl_2$)=778 nm).

Example 4

N,N'-Bis(2,6-diisopropylphenyl)-1,6,11,16-tetra(2,6-diisopropylphenoxy)-8,18-and-8,19-dibromoquaterrylene-3,4:13,14-tetracarboximide (Ia4)

A mixture of 18.0 g (13 mmol) of an approximately equal mixture of N,N'-bis(2,6-diisopropylphenyl)-1,6,8,11,16,18- and -1,6,8,11,16,19-hexabromoquaterrylene-3,4:13,14-tetracarboximide, 640 ml of N-methylpyrrolidone, 9.18 g (52 mmol) of 2,6-diisopropylphenol and 4.34 g (31 mmol) of potassium carbonate was heated to 80° C. and stirred at this temperature for 27 h.

After cooling to room temperature, the reaction mixture was precipitated in 2 l of 10% by weight sulfuric acid. The product was filtered off, washed first in portions with a total of 500 ml of 10% by weight sulfuric acid and then with ethanol, and dried under reduced pressure.

22.1 g (quantitative conversion) of the rylene derivative mixture Ia4 were obtained in the form of a green solid which was further purified by subjecting it to column chromatography on silica gel with a toluene/methylene chloride mixture (9:1) as the eluent.

Example 5

N-(2,6-Diisopropylphenyl)-9-(2,6-diisopropylphenoxy)perylene-3,4-dicarboximide (Ia5)

A mixture of 7.0 g (25 mmol) of N-(2,6-diisopropylphenyl)-9-bromoperylene-3,4-dicarboximide, 2.3 g (25 mmol) of 2,6-diisopropylphenol, 100 ml of N-methylpyrrolidone and 3.45 g (50 mmol) of potassium carbonate was heated to 100° C. for 3 h. After cooling to room temperature, 17 ml of water were added. The precipitated product was filtered off, washed first with 135 ml of 5% by weight sulfuric acid and then to neutrality with water, and dried under reduced pressure.

7.7 g (50%) of the rylene derivative Ia5 were obtained in the form of a violet solid which was further purified by filtering through silica gel with a toluene/ethyl acetate mixture (60:1) as the eluent.

$R_f$ value (60:1 toluene/ethyl acetate)=0.24.

Example 6

N,N'-Bis(2,6-diisopropylphenyl)-1,6,9,14-tetra(2,6-dimethylthiophenoxy)-terrylene-3,4:11,12-tetracarboximide (Ia6)

A solution of 0.8 g (0.7 mmol) of N,N'-bis(2,6-diisopropylphenyl)-1,6,9,14-tetrabromoterrylene-3,4:11,12-tetracarboximide in 50 ml of N-methylpyrrolidone was admixed with 0.4 g (2.8 mmol) of 2,6-dimethylthiophenol and 0.57 g (7 mmol) of potassium carbonate, and heated to 40° C. After stirring at 40° C. for 4 hours, 80 ml of 5% by weight sulfuric acid were added. The precipitated product was filtered off, washed successively with water, 2% by weight sodium hydroxide solution, water and ethanol, and dried under reduced pressure.

1.1 g (quantitative conversion) of Ia6 were obtained in the form of a green solid which was further purified by subjecting it to column chromatography on silica gel with toluene as the eluent.

$R_f$ value (10:1 toluene/ethyl acetate): 0.69;
Absorption: $\lambda_{max}$ ($CH_2Cl_2$)=702 nm; material extinction $E=60\,l\,g^{-1}\,cm^{-1}$;
Emission: $\lambda_{max}$ ($CH_2Cl_2$)=757 nm; weak fluorescence.

Example 7

N,N'-Bis(2,6-diisopropylphenyl)-1,6,11,16-tetra(2,6-diisopropylphenoxy)-8,18- and -8,19-dipiperidylquaterrylene-3,4:13,14-tetracarboximide (Ia7)

A mixture of 0.6 g (0.3 mmol) of the rylene derivative mixture which has been obtained in example 4 and purified by column chromatography and 5.3 g (6.2 ml, 62 mmol) of piperidine was heated in an oil bath heated to 90° C. for 120 h. After cooling to room temperature, the reaction mixture was precipitated in a mixture of 30 ml of methanol and 30 ml of water. The product was filtered off, washed with 11 ml of methanol, stirred in 15 ml of 15% by weight sulfuric acid for 3 h, then filtered off again and washed to neutrality with water.

0.54 g (90%) of the rylene derivative mixture Ia7 was obtained in the form of a green solid which, according to Maldi-MS, also comprised minor amounts of tetraphenoxymonopiperidylmonobromo derivative and tetraphenoxymonopiperidyl derivative.

Absorption: $\lambda_{max}$ (N-methylpyrrolidon)=822 nm; material extinction $E=34.4\,l\,g^{-1}\,cm^{-1}$.

What is claimed is:
1. A rylene derivative of the general formula Ia

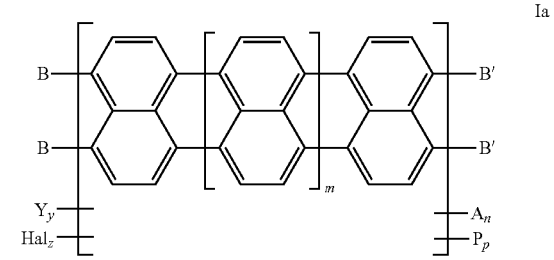

in which the variables are each defined as follows:
B are joined together with formation of a six-membered ring to give a radical of the formula (b)

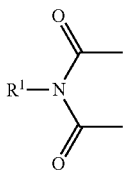

B', independently of B, are joined together with formation of a six-membered ring to give a radical of the formula (b)

A is a radical of the formula

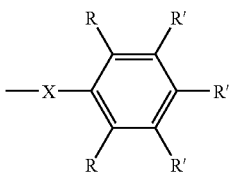

where the A radicals may be the same or different when n>1;

Y is a (thio)phenoxy radical of the formula

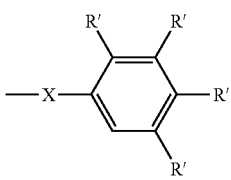

where the Y radicals may be the same or different when y>1;

X is —O— or —S—;

R are identical or different radicals:
(i) $C_1$-$C_{30}$-alkyl which has no more than one tertiary carbon atom in the 1-position and whose carbon chain may be interrupted by one or more —O—, —S—, —$NR^2$—, —C≡C—, —$CR^2$=$CR^2$— and/or —CO— moieties and which may be mono- or polysubstituted by $C_1$-$C_{12}$-alkoxy, hydroxy and/or halogen;
(ii) $C_3$-$C_8$-cycloalkyl which has no more than one tertiary carbon atom in the 1-position and whose carbon skeleton may be interrupted by one or more —O—, —S—, —$NR^2$—, —$CR^2$=$CR^2$— and/or —CO— moieties and which may be mono- or polysubstituted by $C_1$-$C_{18}$-alkyl, $C_1$-$C_{12}$-alkoxy and/or $C_1$-$C_6$-alkylthio;
(iii) aryl or hetaryl, to each of which may be fused further saturated or unsaturated 5- to 7-membered rings whose carbon skeleton may be interrupted by one or more —O—, —S—, —$NR^2$—, —N=$CR^2$—, —$CR^2$=$CR^2$—, —CO—, —SO— and/or —$SO_2$— moieties, where the entire ring system may be mono- or polysubstituted by $C_1$-$C_{18}$-alkyl, $C_1$-$C_{12}$-alkoxy, —C≡$CR^2$, —$CR^2$=$CR^2{}_2$, hydroxy, halogen, —$NR^3R^4$, —$NR^3COR^4$, —$CONR^3R^4$, —$SO_2NR^3R^4$, —$COOR^3$ and/or —$SO_3R^3$;
(iv) a —U-aryl radical which may be mono- or polysubstituted by the above radicals specified as substituents for the aryl radicals (iii), where U is an —O—, —S—, —$NR^2$—, —CO—, —SO— or —$SO_2$— moiety;
(v) $C_1$-$C_{12}$-alkoxy, $C_1$-$C_6$-alkylthio, —C≡$CR^2$, —$CR^2$=$CR^2{}_2$, hydroxy, mercapto, halogen, cyano, nitro, —$NR^3R^4$, —$NR^3COR^4$, —$CONR^3R^4$, —$SO_2NR^3R^4$, —$COOR^3$ or —$SO_3R^3$;

R' are identical or different radicals:
hydrogen;
one of the radicals specified for R (i), (ii), (iii), (iv) and (v), where the alkyl radicals (i) and the cycloalkyl radicals (ii) may have a tertiary carbon atom in the 1-position;

P is a 5- to 9-membered ring which is bonded via a nitrogen atom and whose carbon chain may be interrupted by one or more —O—, —S—, —$NR^2$—, —CO— and/or —$SO_2$-moieties, to each of which may be fused one or two unsaturated or saturated 4- to 8-membered rings whose carbon chain may likewise be interrupted by these moieties and/or —N=, where the entire ring system may be mono- or polysubstituted by: hydroxy, nitro, —$NR^3R^4$, —$COOR^3$, —$CONR^3R^4$ and/or —$NR^2COR^3$;

$C_1$-$C_{30}$-alkyl whose carbon chain may be interrupted by one or more —O—, —S—, —$NR^2$—, —CO— and/or —$SO_2$— moieties and which may be mono- or polysubstituted by cyano, hydroxy, nitro, $C_1$-$C_6$-alkoxy, —$COOR^3$, —$CONR^3R^4$, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;

$C_5$-$C_8$-cycloalkyl whose carbon skeleton may be interrupted by one or more —O—, —S— and/or —$NR^2$— moieties and/or which may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, nitro, halogen, —$CONR^3R^4$, —$NR^3COR^4$, —$SO_3R^3$, —$SO_2NR^3R^4$ and/or aryl- or hetarylazo, each of which may be mono- or polysubstituted by $C_1$-$C_{10}$-alkyl, $C_1$-$C_6$-alkoxy and/or cyano, where the P radicals may be the same or different when p>1;

Hal is fluorine, chlorine, bromine or iodine, $R^1$ is hydrogen;
$C_1$-$C_{30}$-alkyl whose carbon chain may be interrupted by one or more —O—, —S—, —$NR^2$—, —N=$CR^2$—, —C≡C—, —$CR^2$=$CR^2$—, —CO—, —SO— and/or —$SO_2$— moieties and which may be mono- or polysubstituted by the radicals specified for R (ii), (iii), (iv) and/or (v);

$C_3$-$C_8$-cycloalkyl to which may be fused further saturated or unsaturated 5- to 7-membered rings whose carbon skeleton may be interrupted by one or more —O—, —S—, —N=$CR^2$—, —$CR^2$=$CR^2$—, —CO—, —SO— and/or —$SO_2$— moieties, where the entire ring system may be mono- or polysubstituted by the radicals specified for R (i), (ii), (iii), (iv) and/or (v);

aryl or hetaryl, to each of which may be fused further saturated or unsaturated, 5- to 7-membered rings whose carbon skeleton may be interrupted by one or more —O—, —S—, —NR+2-, —N=$CR^2$—, —$CR^2$=$CR^2$—, —CO—, —SO— and/or —$SO_2$- moieties, where the entire ring system may be mono- or polysubstituted by the radicals specified for R (i), (ii), (iii), (iv), (v) and/or aryl- and/or hetarylazo, each of which may be mono- or polysubstituted by $C_1$-$C_{10}$-alkyl, $C_1$-$C_6$-alkoxy and/or cyano, where the $R^1$ radicals may be the same or different when they occur more than once in the formula Ia;

$R^2$ is hydrogen or $C_1$-$C_{18}$-alkyl;

R³, R⁴ are each independently hydrogen;
  $C_1$-$C_{18}$-alkyl which may be mono- or polysubstituted by $C_1$-$C_6$-alkoxy, hydroxy, halogen and/or cyano;
  aryl or hetaryl, each of which may be mono- or polysubstituted by $C_1$-$C_6$-alkyl and/or the above radicals specified as substituents for alkyl;
m is 0, 1 or 2;
n is from 1 to 8;
p is from 0 to 6 where n+p≦8;
y is from 0 to 7 where n+p+y≦8;
z is from 0 to 8 where n+p+y+z≦10.

2. A rylene derivative according to claim 1 of the general formula Ia

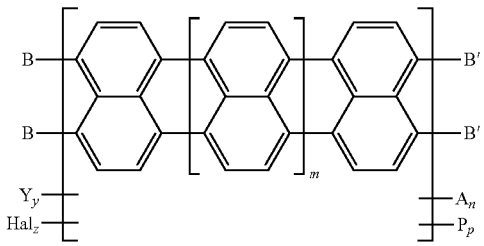

in which the variables are each defined as follows:
B are joined together with formation of a six-membered ring to give a radical of the formula (b)

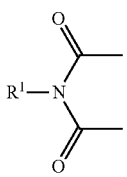

B', independently of B, are joined together with formation of a six-membered ring to give a radical of the formula (b)
A is a radical of the formula

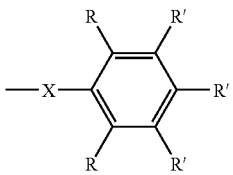

where the A radicals may be the same or different when n>1;
Y is a (thio)phenoxy radical of the formula

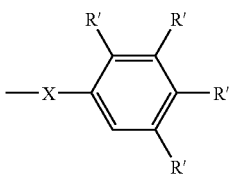

where the Y radicals may be the same or different when y>1;
X is —O— or —S—;
R are identical or different radicals:
  (i) $C_1$-$C_{30}$-alkyl which does not have a tertiary carbon atom in the 1-position and whose carbon chain may be interrupted by one or more —O—, —S—, —NR²—, —C≡C—, —CR²=CR²— and/or —CO— moieties and which may be mono- or polysubstituted by $C_1$-$C_{12}$-alkoxy, hydroxy and/or halogen;
  (ii) $C_3$-$C_8$-cycloalkyl which does not have a tertiary carbon atom in the 1-position and whose carbon skeleton may be interrupted by one or more —O—, —S—, —NR²—, —CR²=CR²— and/or —CO— moieties and which may be mono- or polysubstituted by $C_1$-$C_{18}$-alkyl, $C_1$-$C_{12}$-alkoxy and/or $C_1$-$C_6$-alkylthio;
  (iii) aryl or hetaryl, to each of which may be fused further saturated or unsaturated 5- to 7-membered rings whose carbon skeleton may be interrupted by one or more —O—, —S—, —NR²—, —N=CR²—, —CR²=CR²—, —CO—, —SO— and/or —SO₂— moieties, where the entire ring system may be mono- or polysubstituted by $C_1$-$C_{18}$-alkyl, $C_1$-$C_{12}$-alkoxy, —C≡CR², —CR²=CR²₂, hydroxy, halogen, —NR³R⁴, —NR³COR⁴, —CONR³R⁴, —SO₂NR³R⁴, —COOR³ and/or —SO₃R³;
  (iv) a —U-aryl radical which may be mono- or polysubstituted by the above radicals specified as substituents for the aryl radicals (iii), where U is an —O—, —S—, —NR²—, —CO—, —SO— or —SO₂— moiety;
  (v) $C_1$-$C_{12}$-alkoxy, $C_1$-$C_6$-alkylthio, —C≡CR², —CR²=CR²₂, hydroxy, mercapto, halogen, cyano, nitro, —NR³R⁴, —NR³COR⁴, —CONR³R⁴, —SO₂NR³R⁴, —COOR³ or —SO₃R³;
R' are identical or different radicals:
  hydrogen;
  one of the radicals specified for R (i), (ii), (iii), (iv) and (v), where the alkyl radicals (i) and the cycloalkyl radicals (ii) may have a tertiary carbon atom in the 1-position;
P is a 5- to 9-membered ring which is bonded via a nitrogen atom and whose carbon chain may be interrupted by one or more —O—, —S—, —NR²—, —CO— and/or —SO₂— moieties, to each of which may be fused one or two unsaturated or saturated 4- to 8-membered rings whose carbon chain may likewise be interrupted by these moieties and/or —N=, where the entire ring system may be mono- or polysubstituted by: hydroxy, nitro, —NR³R⁴, —COOR³, —CONR³R⁴ and/or —NR²COR³;
  $C_1$-$C_{30}$-alkyl whose carbon chain may be interrupted by one or more —O—, —S—, —NR²—, —CO— and/or —SO₂— moieties and which may be mono- or polysubstituted by cyano, hydroxy, nitro, $C_1$-$C_6$-alkoxy, —COOR³, —CONR³R⁴, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;
  $C_5$-$C_8$-cycloalkyl whose carbon skeleton may be interrupted by one or more —O—, —S— and/or —NR²— moieties and/or which may be mono- or polysubstituted by $C_1$-$C_6$-alkyl;
  aryl or hetaryl, each of which may be mono- or polysubstituted by $C_1$-$C_{18}$-alkyl, $C_1$-$C_6$-alkoxy, cyano, nitro, halogen, —CONR³R⁴, —NR³COR⁴, —SO₃R³, —SO₂NR³R⁴ and/or aryl- or hetarylazo, each of which may be mono- or polysubstituted by $C_1$-$C_{10}$-alkyl, $C_1$-$C_6$-alkoxy and/or cyano,
  where the P radicals may be the same or different when p>1;
Hal is fluorine, chlorine, bromine or iodine,
R¹ is hydrogen;

$C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by the radicals specified for R (ii), (iii), (iv) and/or (v);

$C_3$-$C_8$-cycloalkyl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the radicals specified for R (i), (ii), (iii), (iv) and/or (v);

aryl or hetaryl, to each of which may be fused further saturated or unsaturated, 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$- moieties, where the entire ring system may be mono- or polysubstituted by the radicals specified for R (i), (ii), (iii), (iv), (v) and/or aryl- and/or hetarylazo, each of which may be mono- or polysubstituted by $C_1$-$C_{10}$-alkyl, $C_1$-$C_6$-alkoxy and/or cyano, where the R$^1$ radicals may be the same or different when they occur more than once in the formula Ia;

R$^2$ is hydrogen or $C_1$-$C_{18}$-alkyl;

R$^3$, R$^4$ are each independently hydrogen;
$C_1$-$C_{18}$-alkyl which may be mono- or polysubstituted by $C_1$-$C_6$-alkoxy, hydroxy, halogen and/or cyano;
aryl or hetaryl, each of which may be mono- or polysubstituted by $C_1$-$C_6$-alkyl and/or the above radicals specified as substituents for alkyl;

m is 0, 1 or 2;
n is from 1 to 8;
p is from 0 to 6 where n+p≦8;
y is from 0 to 7 where n+p+y≦8;
z is from 0 to 8 where n+p+y+z≦10.

3. A rylene derivative of the general formula Ib

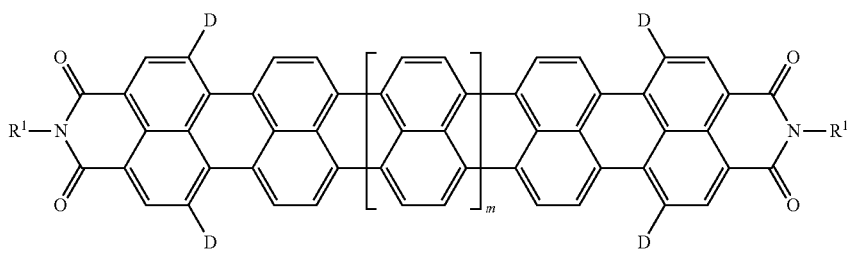

in which the variables are each defined as follows:

D are identical or different radicals:
hydrogen, an A radical or a Y radical, where at least one of the D radicals is an A radical, A is a radical of the formula

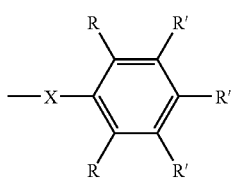

Y is a (thio)phenoxy radical of the formula

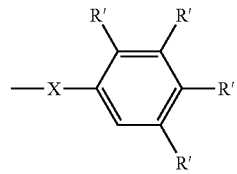

X is —O— or —S—;

R are identical or different radicals:
(i) $C_1$-$C_{30}$-alkyl which does not have a tertiary carbon atom in the 1-position and whose carbon chain may be interrupted by one or more —O—, —S—, —NR$^2$—, —C≡C—, —CR$^2$=CR$^2$— and/or —CO— moieties and which may be mono- or polysubstituted by $C_1$-$C_{12}$-alkoxy, hydroxy and/or halogen;

(ii) $C_3$-$C_8$-cycloalkyl which does not have a tertiary carbon atom in the 1-position and whose carbon skeleton may be interrupted by one or more —O—, —S—, —NR$^2$—, —CR$^2$=CR$^2$— and/or —CO— moieties and which may be mono- or polysubstituted by $C_1$-$C_{18}$-alkyl, $C_1$-$C_{12}$-alkoxy and/or $C_1$-$C_6$-alkylthio;

(iii) aryl or hetaryl, to each of which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by $C_1$-$C_{18}$-alkyl, $C_1$-$C_{12}$-alkoxy, —C≡CR$^2$, —CR$^2$=CR$^2$_2, hydroxy, halogen, —NR$^3$R$^4$, —NR$^3$COR$^4$, —CONR$^3$R$^4$, —SO$_2$NR$^3$R$^4$, —COOR$^3$ and/or —SO$_3$R$^3$;

(iv) a —U-aryl radical which may be mono- or polysubstituted by the above radicals specified as substituents for the aryl radicals (iii), where U is an —O—, —S—, —NR$^2$—, —CO—, —SO— or —SO$_2$— moiety;

(v) $C_1$-$C_{12}$-alkoxy, $C_1$-$C_6$-alkylthio, —C≡CR$^2$, —CR$^2$=CR$^2$_2, hydroxy, mercapto, halogen, cyano, nitro, —NR$^3$R$^4$, —NR$^3$COR$^4$, —CONR$^3$R$^4$, —SO$_2$NR$^3$R$^4$, —COOR$^3$ or —SO$_3$R$^3$;

R' are identical or different radicals:
hydrogen;
one of the radicals specified for R (i), (ii), (iii), (iv) and (v), where the alkyl radicals (i) and the cycloalkyl radicals (ii) may have a tertiary carbon atom in the 1-position;

R$^1$ is hydrogen;
$C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by the radicals specified for R (ii), (ii), (iv) and/or (v);

C$_3$-C$_8$-cycloalkyl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the radicals specified for R (i), (ii), (iii), (iv) and/or (v);

aryl or hetaryl, to each of which may be fused further saturated or unsaturated, 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$- moieties, where the entire ring system may be mono- or polysubstituted by the radicals specified for R (i), (ii), (iii), (iv), (v) and/or aryl- and/or hetarylazo, each of which may be mono- or polysubstituted by C$_1$-C$_{10}$-alkyl, C$_1$-C$_6$-alkoxy and/or cyano, where the R$^1$ radicals may be the same or different when they occur more than once in the formula Ib;

R$^2$ is hydrogen or C$_1$-C$_{18}$-alkyl;

R$^3$, R$^4$ are each independently hydrogen;

C$_1$-C$_{18}$-alkyl which may be mono- or polysubstituted by C$_1$-C$_6$-alkoxy, hydroxy, halogen and/or cyano;

aryl or hetaryl, each of which may be mono- or polysubstituted by C$_1$-C$_6$-alkyl and/or the above radicals specified as substituents for alkyl;

m is 1 or 2.

4. The method for coloring organic and inorganic materials comprising the step of applying rylene derivatives according to claim 1.

5. The method according to claim 4, wherein the organic materials are coatings, printing inks or plastics.

6. The method of producing aqueous polymer dispersions which absorb and/or emit electromagnetic radiation comprising the step of applying rylene derivatives according to claim 1.

7. The method of preparing markings and inscriptions which absorb infrared light and are invisible to the human eye comprising the step of applying rylene derivatives according to claim 1.

8. The method of preparing infrared absorbers for heat management comprising the step of applying rylene derivatives according to claim 1.

9. The method of fusion treatment of plastics parts comprising the step of applying rylene derivatives according to claim 1 as IR laser beam-absorbent materials.

10. The method of laser marking and laser inscription comprising the step of applying rylene derivatives according to claim 1.

11. The method of preparing organic electronics comprising the step of applying rylene derivatives according to claim 1 as semiconductors.

12. The method of preparing display applications comprising the step of applying rylene derivatives according to claim 1 as filters or emitters.

13. The method of preparing chemiluminescence applications comprising the step of applying rylene derivatives according to claim 1 as emitters.

14. The method of detection comprising the step of applying rylene derivatives according to claim 1 as labeling groups.

15. The method of photovoltaics comprising the step of applying rylene derivatives according to claim 1 as active components.

16. The method for coloring organic and inorganic materials comprising the step of applying rylene derivatives according to claim 3.

17. The method according to claim 16, wherein the organic materials are coatings, printing inks or plastics.

18. The method of producing aqueous polymer dispersions which absorb and/or emit electromagnetic radiation comprising the step of applying rylene derivatives according to claim 3.

19. The method of preparing markings and inscriptions which absorb infrared light and are invisible to the human eye comprising the step of applying rylene derivatives according to claim 3.

20. The method of preparing infrared absorbers for heat management comprising the step of applying rylene derivatives according to claim 3.

21. The method of fusion treatment of plastics parts comprising the step of applying rylene derivatives according to claim 3 as IR laser beam-absorbent materials.

22. The method of laser marking and laser inscription comprising the step of applying rylene derivatives according to claim 3.

23. The method of preparing organic electronics comprising the step of applying rylene derivatives according to claim 3 as semiconductors.

24. The method of preparing display applications comprising the step of applying rylene derivatives according to claim 3 as filters or emitters.

25. The method of preparing chemiluminescence applications comprising the step of applying rylene derivatives according to claim 3 as emitters.

26. The method of detection comprising the step of applying rylene derivatives according to claim 3 as labeling groups.

27. The method of photovoltaics comprising the step of applying rylene derivatives according to claim 3 as active components.

* * * * *